(12) United States Patent
Papathanasiou et al.

(10) Patent No.: US 12,019,000 B2
(45) Date of Patent: Jun. 25, 2024

(54) SYSTEMS AND METHODS FOR CAPTURING CELLS

(71) Applicants: Dana-Farber Cancer Institute, Inc., Boston, MA (US); The Broad Institute, Inc., Cambridge, MA (US)

(72) Inventors: Stamatios Papathanasiou, Boston, MA (US); Huaibin Zhang, Cambridge, MA (US)

(73) Assignees: DANA-FARBER CANCER INSTITUTE, INC., Boston, MA (US); THE BROAD INSTITUTE, INC., Cambridge, MA (US)

( * ) Notice: Subject to any disclaimer, the term of this patent is extended or adjusted under 35 U.S.C. 154(b) by 947 days.

(21) Appl. No.: 17/040,319

(22) PCT Filed: Mar. 22, 2019

(86) PCT No.: PCT/US2019/023696
§ 371 (c)(1),
(2) Date: Sep. 22, 2020

(87) PCT Pub. No.: WO2019/183554
PCT Pub. Date: Sep. 26, 2019

(65) Prior Publication Data
US 2021/0088422 A1    Mar. 25, 2021

Related U.S. Application Data

(60) Provisional application No. 62/742,811, filed on Oct. 8, 2018, provisional application No. 62/647,535, filed on Mar. 23, 2018.

(51) Int. Cl.
*G01N 1/28* (2006.01)
*G01N 21/64* (2006.01)
(Continued)

(52) U.S. Cl.
CPC ......... *G01N 1/286* (2013.01); *G01N 21/6452* (2013.01); *G01N 21/6456* (2013.01);
(Continued)

(58) Field of Classification Search
CPC ............... G01N 1/286; G01N 21/6452; G01N 21/6456; G01N 33/5005; G01N 2001/2886; G02B 21/34
See application file for complete search history.

(56) References Cited

U.S. PATENT DOCUMENTS

2008/0069737 A1* 3/2008 Fasulka ................ G02B 21/34
422/400
2008/0199929 A1* 8/2008 Yeung ..................... G01N 1/30
359/368

(Continued)

FOREIGN PATENT DOCUMENTS

WO    WO 2008/034833 A2    3/2008
WO    WO 2010/020876 A2    2/2010
(Continued)

OTHER PUBLICATIONS

International Search Report and Written Opinion dated Jun. 19, 2019 in connection with International Application No. PCT/US2019/023696.

(Continued)

*Primary Examiner* — Peter J Macchiarolo
*Assistant Examiner* — John M Royston
(74) *Attorney, Agent, or Firm* — Mueting Raasch Group

(57) ABSTRACT

Systems and methods for capturing cells of interest from a larger group of cells are provided. In some embodiments, the cells are held within cell culture media inside a chamber during laser dissection.

21 Claims, 28 Drawing Sheets

(51) Int. Cl.
*G01N 33/50* (2006.01)
*G02B 21/34* (2006.01)

(52) U.S. Cl.
CPC ......... *G01N 33/5005* (2013.01); *G02B 21/34* (2013.01); *G01N 2001/2886* (2013.01)

(56) References Cited

U.S. PATENT DOCUMENTS

| | | | | |
|---|---|---|---|---|
| 2011/0287470 | A1* | 11/2011 | Stoppini | C12M 25/01 506/26 |
| 2015/0125363 | A1 | 5/2015 | Schlaudraff | |
| 2016/0305855 | A1* | 10/2016 | Richardson | G01N 1/286 |
| 2016/0314583 | A1* | 10/2016 | Couch | H04N 23/56 |

FOREIGN PATENT DOCUMENTS

| | | |
|---|---|---|
| WO | WO 2010/138960 A2 | 12/2010 |
| WO | WO 2015/095603 A1 | 6/2015 |

OTHER PUBLICATIONS

International Preliminary Report on Patentability dated Oct. 8, 2020 in connection with International Application No. PCT/US2019/023696.
Bouchard et al., Laser Capture Microdissection of Neurons from Differentiated Human Neuroprogenitor Cells in Culture. Journal of Visualized Experiments. Sep. 16, 2013; 79(e50487):1-8.
Gilbrich-Wille, Application-specific Consumables for Laser Microdissection. Learn & Share. Leica Microsystems Tutorial. May 4, 2015; 10 pages.
Gilbrich-Wille, Cell Cultures and Laser Microdissection. Learn & Share. Leica Microsystems Tutorial. Oct. 7, 2011; 8 pages.
Mackenzie, "cGAS surveillance of micronuclei links genome instability to innate immunity," Aug. 24, 2017, *Nature*, 548(7668): 461-65.
Papathanasiou, "Heritable transcriptional defects from aberrations of nuclear architecture," Jul. 6, 2023, *Nature*, 619: 184, 47 pages.
Veritas™ Microdissection Instrument User Guide 13553-00, Version C. Arcturus. © 2003-2005 Arcturus Bioscience, Inc.: Mountain View, CA. 126 pages.

* cited by examiner cDNA library generation efficiency

Assessed by a. cDNA library concentration (using Qubit) and b. cDNA fragment size distribution (using Bioanalyzer)

TABLE 1: Success rates with prior art cell capturing system

| Condition | % Successful | Successful |
|---|---|---|
| Protocol 1 | 9 | 5/54 |
| Protocol 2 | 39 | 9/23 |
| Protocol 3 | 55 | 5/9 |
| Protocol 4 | 63 | 74/117 |
| Protocol 5 | 66 | 8/12 |
| Protocol 6 | 50 | 4/8 |

TABLE 2A: Success rates with new cell capturing system

| Condition | % Successful | Successful |
|---|---|---|
| Protocol 6 | 89 | 140/158 |

TABLE 2B: Success rates with new cell capturing system, increased sample size

| Condition | % Successful | Successful |
|---|---|---|
| half / 21 cycles / frozen | 91 | 287/315 |

FIG. 8

Sequencing QC

Demultiplexed sequencing files were aligned
to the transcriptome using STAR software Calculated based on 287 sequenced samples
(in MiSeq or HiSeq 2000)

LCC-scRNAseq

- Avg gene # >=1 read: 7657
- Avg gene # >=5 reads: 6400
- Avg gene # >=5 reads: 5602

FIG. 9B

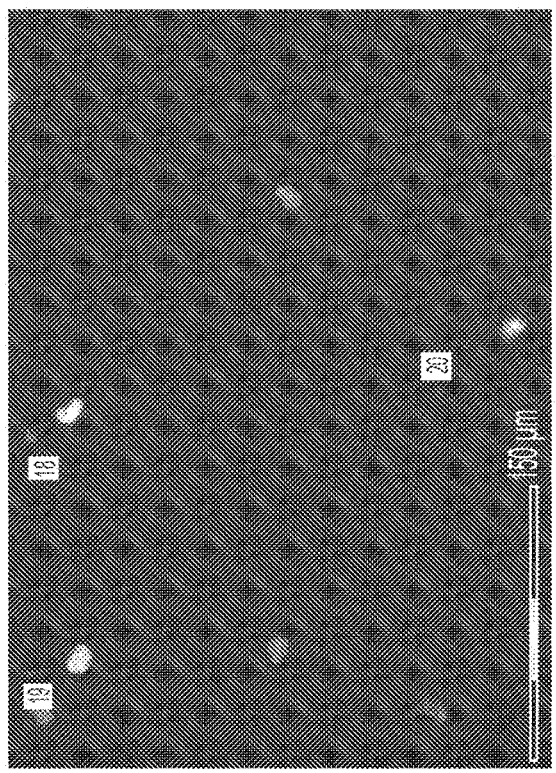
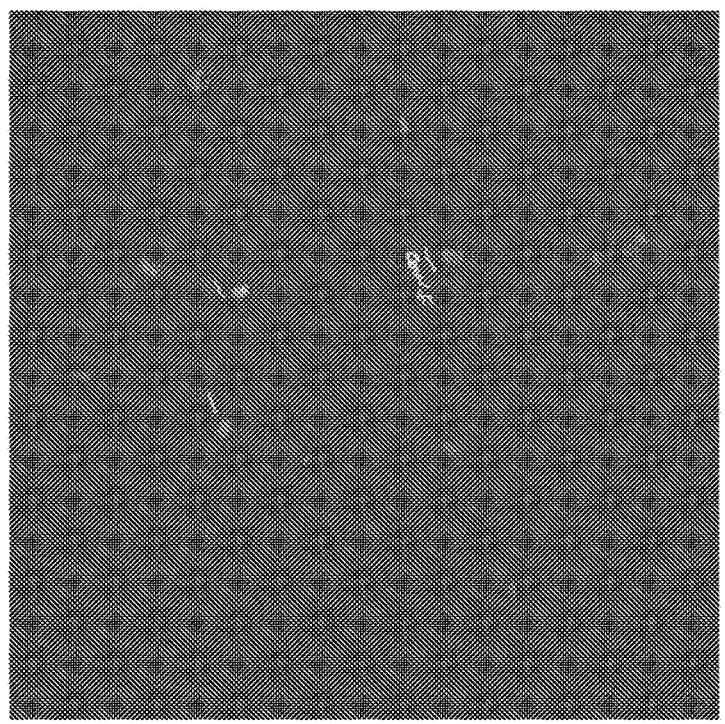
FIG. 16B
FIG. 16A

Table 3

| Exp_name | Samples Name | WGA method | DNA concentration (ng/ul) | Total DNA (ug) |
|---|---|---|---|---|
| 180101_LCM | 180101_C8 | MDA | 77.2 | 7.7 |
| 180101_LCM | 180101_D8 | MDA | 37 | 3.7 |
| 180101_LCM | 180101_E8 | MDA | 30.2 | 3.0 |
| 180101_LCM | 180101_F8 | MDA | 87.8 | 8.8 |
| 180101_LCM | 180101_G8 | MDA | 77.4 | 7.7 |
| 180101_LCM | 180101_H8 | MDA | 60.4 | 6.0 |

FIG. 22

Table 4

| id | TOTAL_READS | PCT_PF_READS_ALIGNED | PCT_CHIMERAS |
|---|---|---|---|
| A_S19 | 1960458 | 0.997658 | 0.010635 |
| A_S23 | 2674770 | 0.997262 | 0.011285 |
| B_S24 | 1672442 | 0.997699 | 0.010851 |
| C_S20 | 1178232 | 0.997919 | 0.012195 |
| F_S21 | 1941992 | 0.997634 | 0.010702 |
| H_S22 | 2071064 | 0.997744 | 0.011182 |

FIG. 23

Table 5 primary mouse tail fibroblasts

| Sample | N_unmapped (%) | geneCounts (%) | >=1 read | >=5 reads | >=10 reads | totalReads |
|---|---|---|---|---|---|---|
| 181013B_5B | 8 | 73 | 10775 | 8692 | 7604 | 1403042 |
| 181013B_5C | 9 | 71 | 11354 | 8980 | 7789 | 1798342 |
| 181013B_5F | 10 | 73 | 10742 | 8568 | 7470 | 1728874 |
| 181013B_5A | 6 | 77 | 10438 | 9420 | 7444 | 1441077 |
| 181013B_5G | 7 | 74 | 10262 | 8279 | 7399 | 1569164 |
| AVG: | 8 | 74 | 10714 | 23747 | 7541 | |

FIG. 27

SYSTEMS AND METHODS FOR CAPTURING CELLS

RELATED APPLICATIONS

This application is a national stage filing under 35 U.S.C. § 371 of International Application No. PCT/US2019/023696, filed Mar. 22, 2019, which claims the benefit under 35 U.S.C. § 119(e) to U.S. Provisional Application, U.S. Ser. No. 62/742,811, filed on Oct. 8, 2018, and to U.S. Provisional Application, U.S. Ser. No. 62/647,535, filed on Mar. 23, 2018, each of which is incorporated herein by reference.

TECHNICAL FIELD

Systems and methods for capturing cells of interest from a larger group of cells are described.

SUMMARY

According to one aspect, a system for capturing one or more cells of interest from a group of cells is provided. The system includes, in some embodiments, a cell culture membrane, cell culture media, a plurality of cells on the cell culture membrane and positioned within the cell culture media, a transparent surface in contact with the cell culture media, the cell culture media being positioned between the cell culture membrane and the transparent surface, a microscopic imaging device, a collector positioned closer to the cell culture membrane than to the transparent surface, and a laser source positioned closer to the transparent surface than to the cell culture membrane.

According to another aspect, a method for capturing one or more cells of interest from a group of cells is provided. The method includes, in some embodiments, providing a plurality of cells that are on a cell culture membrane and in cell culture media, covering the plurality of cells and cell culture media with a transparent surface such that the cell culture media is positioned between the cell culture membrane and the transparent surface, imaging the plurality of cells with an imaging device, and shining a laser beam through the transparent surface to cut out a portion of the plurality of cells while the plurality of cells are within the cell media, causing the portion of the plurality of cells to move in a direction away from the transparent surface onto a collector.

According to another aspect, a chamber for capturing one or more cells of interest from a group of cells is provided. The chamber includes, in some embodiments, a ring, a cell culture membrane coupled to the ring, and a transparent surface opposing the cell culture membrane to form a watertight chamber with the ring and the cell culture membrane.

Other advantages and novel features of the present invention will become apparent from the following detailed description of various non-limiting embodiments of the invention when considered in conjunction with the accompanying figures. In cases where the present specification and a document incorporated by reference include conflicting and/or inconsistent disclosure, the present specification shall control. If two or more documents incorporated by reference include conflicting and/or inconsistent disclosure with respect to each other, then the document having the later effective date shall control.

BRIEF DESCRIPTION OF THE DRAWINGS

Non-limiting embodiments of the present invention will be described by way of example with reference to the accompanying figures, which are schematic and are not intended to be drawn to scale. In the figures, each identical or nearly identical component illustrated is typically represented by a single numeral. For purposes of clarity, not every component is labeled in every figure, nor is every component of each embodiment of the invention shown where illustration is not necessary to allow those of ordinary skill in the art to understand the invention. In the figures:

FIGS. 8, 9A and 9B show data demonstrating the overall efficiency and robustness of the cell capturing system in generating high quality single-cell RNA sequencing data;

FIG. 16A shows an image of cells of interest taken by a fluorescent microscope;

FIG. 16B shows an image of the cells of interest of FIG. 16A taken by a laser capture microdissection microscope;

FIGS. 22 and 23 show data demonstrating the overall efficiency and robustness of the cell capturing system in generating high quality single-cell DNA sequencing data;

FIG. 27 is a table showing data demonstrating the overall efficiency and robustness of the cell capturing system with the primary mouse tail fibroblasts.

DETAILED DESCRIPTION

Figure 1:
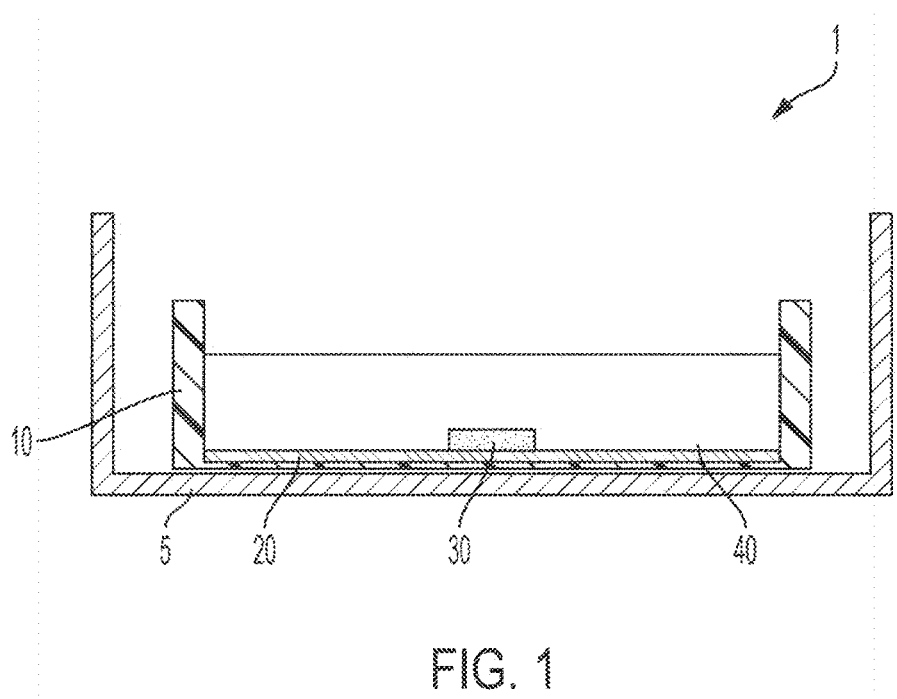
FIG. 1 is a schematic illustration of a conventional chamber setup for laser capture microdissection.

Systems and methods for capturing cells of interest from a larger group of cells are generally described.

Laser capture microdissection is a method used to isolate single cells or groups of cells from their surrounding tissues with the aid of a laser beam, and under microscopic visualization. Captured cells can be placed in a micro centrifuge tube for subsequent molecular analysis. For example, captured cells can be used to generate cDNA libraries to conduct transcriptome, DNA, chromatin/epigenetic, or proteome analyses.

The inventor has appreciated that conventional cell capturing techniques, including conventional laser capture microdissection techniques, can affect the characteristics of the disassociated cells, which may lead to inaccurate data. Mechanical stress to cells can alter gene expression in cells that may result in atypical gene expression profile and/or cellular function. Many conventional laser capture microdissection techniques require removal of all cell culture media from the chamber holding the cells prior to beginning the cell dissociation process. The inventors have appreciated that removal of cell culture media is a time-intensive and laborious process, resulting in low throughput. The inventors have also appreciated that removal of cell culture media may cause cells to lose viability and/or cause stress to the cells, which may affect the characteristics of the cells, such as the transcriptome of the cells. Other methods involve attachment of the capturing device to the membrane where the cells are attached. The inventors have appreciated that such methods may limit throughput and increase contamination risk or failure rate.

The inventors have recognized the need for a system and method of dissociating and capturing specific cells of interest from a larger group of cells without affecting the characteristics of the captured cells. Some embodiments described herein may allow for a method of cell capture that subjects the cells to less perturbation than conventional methods.

According to one aspect, in some embodiments of the cell capturing process, the cells remain in cell culture media during the laser cutting process, rather than removing the media. Such an arrangement may allow the cells to remain in the nutrient-rich media up until the point of capture, helping the captured cells remain viable and healthy for a longer period of time.

Small groups of cells, single cells, and/or individual nuclei may be isolated and captured using the methods described herein.

In some embodiments, live cells of interest can be visualized and immediately captured in lysis buffer or other non-lysis buffer for subsequent analysis allowing for studies directly linking phenotypes with genomics, even at the single-cell level (e.g. single-cell RNA or DNA sequencing). In some embodiments, the system may be adapted for other applications such as epigenetic studies (e.g., ATAC-seq, Hi-C, DNA methylation, Dam-ID, etc.)

In some embodiments, methods described herein permit the ability to correlate between cellular morphology (e.g. using bright field imaging) or cellular processes (e.g. using fluorescent markers and florescence microscopy) with single-cell genomics of cells of interest.

In some embodiments, methods described herein permit the ability to perform single-cell genomics analysis with specific cells of interest upon response to specific treatments or perturbations, based on phenotype.

In some embodiments, methods described herein permit the ability to follow cell lineage by long-term live-imaging and collecting single cells or specific progeny for lineage-related studies. In some embodiments, methods described herein permit capturing and re-culturing of small portions of cells and/or single cells. In some embodiments, relationship information between cells may be maintained due to the ability to directly capture cells from culture without the need for transferring the cells in other setups for isolation (e.g., FACS sorting). In some embodiments, the cell capturing procedure is a contact-free laser catapulting arrangement that decreases potential contamination.

A variety of different cells may be used with the arrangements and methods described herein, e.g., different cell types, cell lines, primary cells, adherent cells, non-adherent cells, any cells that can be cultured, or any other suitable cells. The cells may be from different types of organisms, such as human, mice, worms, yeast, or any other suitable type of organism. The arrangements and methods described herein are not limited to use with single-cell capture, as capturing of colonies or multi-cellular organisms may be performed as well.

A conventional laser capture microdissection arrangement 1 is shown in FIG. 1. The cell of interest 30 is located within a ring 10 along with a group of other cells within liquid cell culture media 40. The cells are positioned on a polyethylene naphthalate (PEN) membrane 20. The membrane 20 is coupled to the ring 10 to form an open-top holding container. A Lumox dish 5 holds the ring 10 in place for imaging and for laser dissection.

Figure 2:
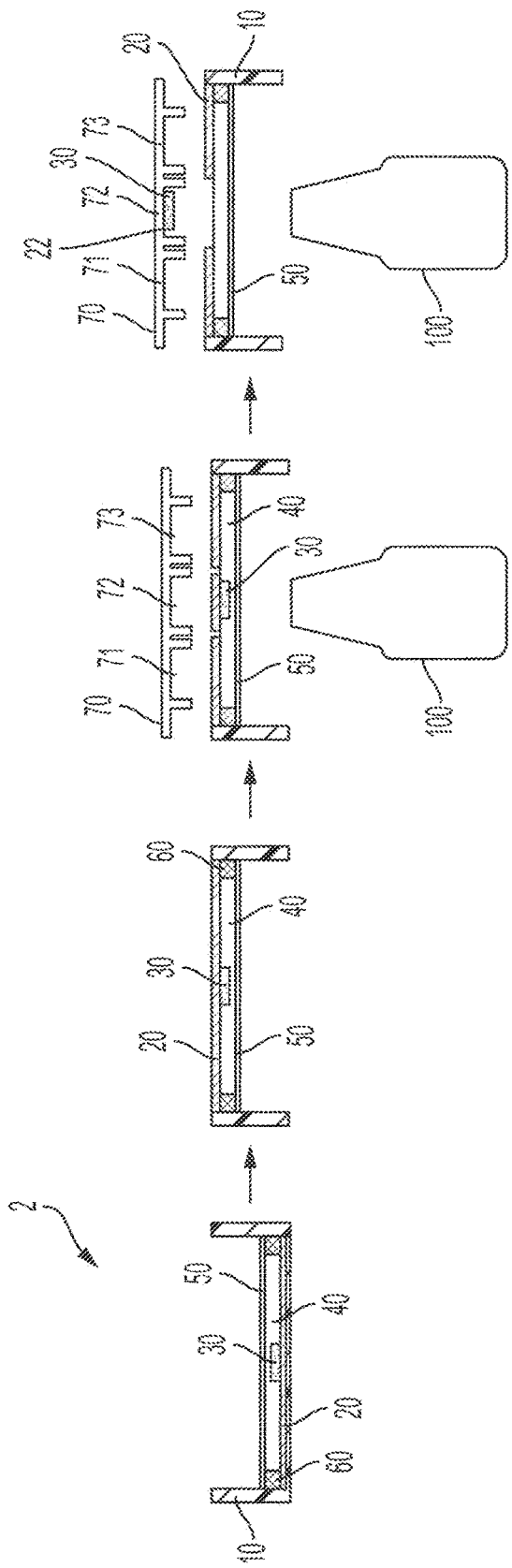
FIG. 2 is a schematic illustration of a novel cell capturing process and chamber setup.

According to one illustrative embodiment, a chamber 2 and associated laser capture microdissection process is shown in FIG. 2. The chamber 2 includes a ring 10 with a cell culture membrane 20 coupled to the ring to form a holding container. Examples of cell culture membranes include, but are not limited to, polyethylene naphthalate (PEN) and polyethylene terephthalate (PET). The cell of interest 30 is positioned on the cell culture membrane along with a group of other cells within liquid cell culture media 40. A transparent surface 50 is added to the construct to form a chamber 2. The transparent surface 50 covers the cells and cell culture media 40. In some embodiments, the transparent surface, ring and cell culture membrane combine to form a sealed chamber that holds in the cell culture media. As shown in step 2 of the FIG. 2 process, when the chamber is flipped upside down, the liquid cell culture media does not escape. In some embodiments, an additional hydrophobic barrier 60 may be added to aid in sealing the chamber 2. The hydrophobic barrier may be a seal applied to the surface of the inner periphery of the ring 10. In some embodiments, the seal is made of polyethylene naphthalate.

In some embodiments, the ring is spanned with the cell culture membrane. In some embodiments, the ring is made of plastic. In some embodiments, the ring is MembraneRing 50 from Carl Zeiss, which is a plastic ring spanned with a cell culture membrane for microdissection. Carl Zeiss instructs users to use MembraneRing 50 exclusively with a Lumox dish for microdissection, but inventors discovered that, surprisingly, in some embodiments, the dish was not needed, e.g. for cell culture, imaging, and/or cell capture. In some embodiments, the transparent surface is placed in contact with the cell culture media. In some embodiments, the transparent surface may be held in place relative to the ring 10 via surface tension arising from the interaction between the transparent surface and the cell culture media. In some embodiments, the volume of cell culture media in the chamber is about 10-100 uL, or about 15-90 uL, or about 20-80 uL, or about 25-70 uL, or about 30-60 uL, or about 35-60 uL, or about 40 uL. The inventors were surprised that, in some embodiments, surface tension alone was sufficient to keep the transparent surface in place and prevent leakage of liquid cell culture media, even when the chamber was turned upside down with the transparent surface at the bottom.

In some embodiments, the transparent surface is a glass coverslip. In some embodiments, the glass coverslip has a 20 mm diameter.

As shown in step 2 of FIG. 2, in some embodiments, the chamber 2 is flipped upside down such that the cell culture membrane 20 is positioned above the transparent surface 50.

Next, as shown in step 3 of FIG. 2, the chamber is positioned between a laser source 100 and a collector 70. The laser source 100 may be positioned beneath the chamber and the capturing plate may be positioned above the chamber. Laser emitted from the laser source 100 first passes through the transparent surface 50 and cuts out the cell 30, causing the cell to catapult away from the laser source and away from the transparent surface 50 toward the collector 70 into the well 72 of the collector 70.

The inventors were surprised that the presence of the transparent surface did not adversely affect microdissection and catapulting/capturing results.

In some embodiments, the collector 70 is a capture plate, e.g., a multi-well plate containing, e.g., 6, 12, 24, 48 or 96 wells. In other embodiments, however, the collector is a single well plate. In some embodiments, the collector is a single cup or a multiple-cup collector.

According to one aspect, the chamber arrangement permits the chamber to be positioned between the laser source and the capturing plate, with the laser source being on the side of the transparent surface, and the capturing plate being on the side of the cell culture membrane. With the capturing plate on the side of the cell culture membrane, the capturing plate is not blocked by the walls of the ring 10, and thus the plate can be held very close to the cell of interest 30. In laser capture microdissection, the capturing plate must be held at a very close distance (e.g. less than or equal to 5 mm distance) to the cell during catapulting for the cell to end up at the proper location on the capturing plate. In conventional arrangements where the cell-holding container is flipped in orientation, the capturing plate faces the side wall of the ring 10, and is blocked by the ring wall from moving to the required close distance to the cell, unless the plate is of a small enough size to fit within the diameter of the ring 10. Standard multi-well plates generally cannot fit within a ring having an inner diameter of about 20 mm. Thus, in conventional laser capture microdissection procedures, a specialized small, single-well plate that can fit within the ring 10 is used. Further, because the plate is limited to a small size, only a single well can fit. The inventors have appreciated that using these specialized single-well plates can, in some embodiments, result in low throughput, as a new single-well plate must be used for each cell capture. In contrast, the chamber arrangement permits the chamber to be used with multi-well plates, and many cells can be captured in quick succession simply by moving the well plate to the appropriate position such that the next empty well is aligned with the cell of interest prior to the laser cutting the cell of interest out from the group of cells.

Figure 3:
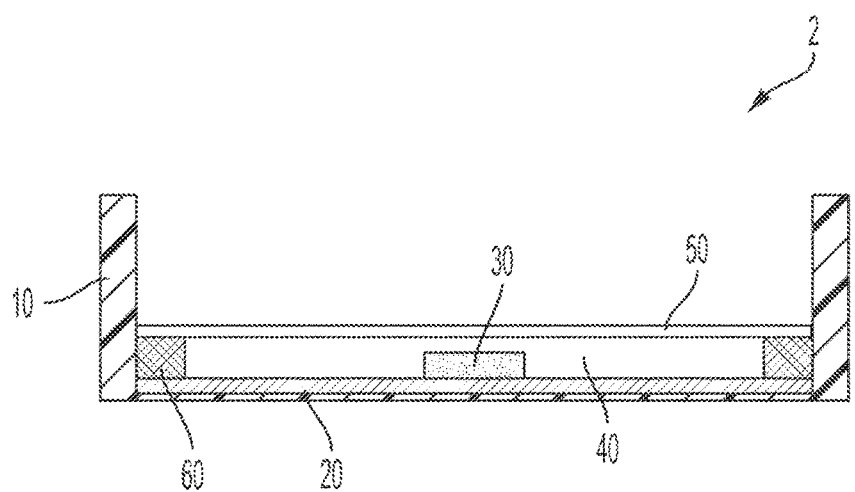
FIG. 3 is a schematic illustration of a chamber setup used in the cell capturing process shown in FIG. 2.

The chamber 2 is shown in greater detail in FIG. 3.

In some embodiments, the chamber provides sufficient cell culture conditions for more than 90 minutes (e.g., using HEPES containing medium in room temperature), as the chamber decreases the amount of liquid media evaporation.

The chamber may be used with existing laser capture microdissection microscopes, such as the Palm Microbeam LCM System (CARL ZEISS), or other cell capturing devices.

Figure 4:
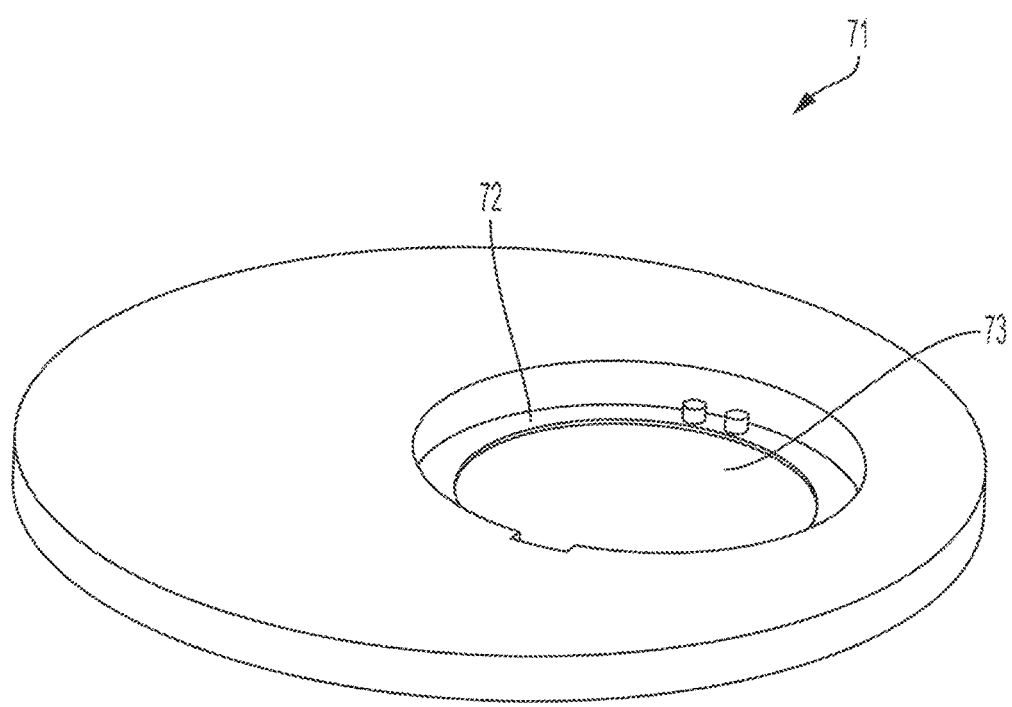
FIG. 4 is an adapter for use with the cell capturing process shown in FIG. 2.
Figure 5:
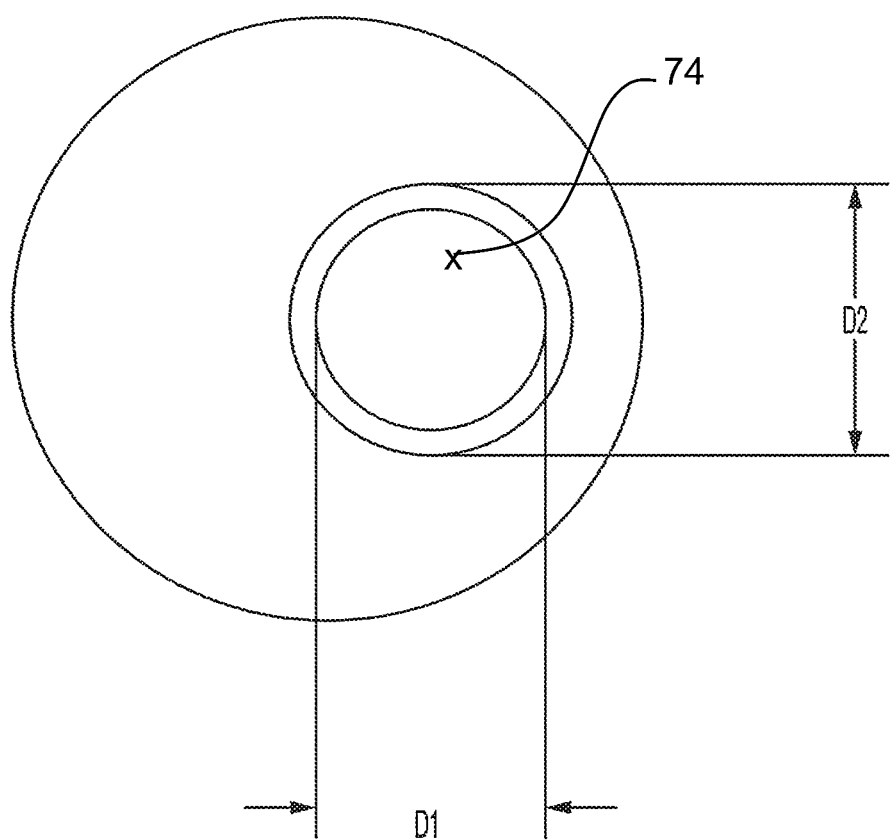
FIG. 5 is a top-down view of the adapter of FIG. 4.

In some embodiments, an adapter can be used to permit use of the chamber with existing laser capture microdissection microscopes or other cell capturing devices. One illustrative embodiment of an adapter 71 is shown in FIGS. 4 and 5. The adapter 71 may include a recessed ledge 72 to hold the ring of the chamber, and may have a through-hole 73 to permit passage of the laser beam. A top-down view of the adapter is shown in FIG. 5. The through-hole may have a diameter D1 of about 20-23 mm, or 21.97 mm. The diameter D2 of the recess may be about 25-29 mm, 27.05 mm, or 50 mm. In some embodiments, the diameter may range from 5-100 mms, 10-50 mms, or any other suitable diameter. The adapter may be 3D printed, molded, or otherwise manufactured using any suitable process.

Figure 6:
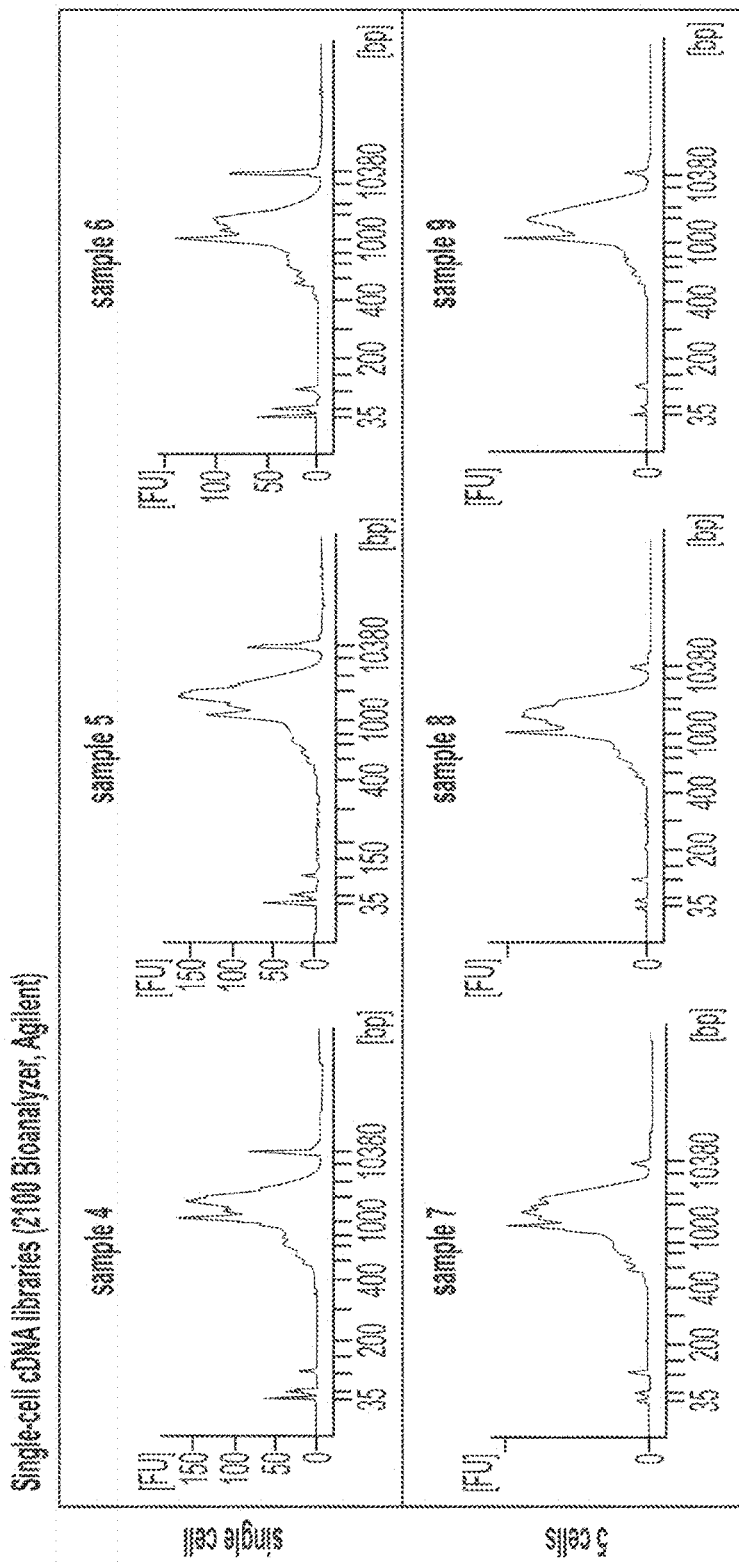
FIG. 6 shows representative fragment size distribution of cDNA libraries generated from cells that were captured using the novel cell capturing system.

The data shown in FIGS. 6-9 illustrate the effectiveness of the cell capturing system described above. FIG. 6 depicts representative fragment size distribution of cDNA libraries analyzed by a Bioanalyzer 2100 instrument. The cDNA libraries shown in the top three panels were generated from single cells and the cDNA libraries shown in the bottom three panels were each generated from five cells. All cells were captured using one embodiment of a cell capturing system described above. The cDNA libraries are of high quality, as the average fragment size is at around 2 kb length, as expected from the human full length RNA. The protocol used to generate these cDNA libraries is called Smart-Seq2, which generates full length transcripts.

It should be appreciated that, in other embodiments, other protocols for generating libraries for single cell RNA sequencing may be used, and is not limited to Smart-Seq2.

Figure 7:
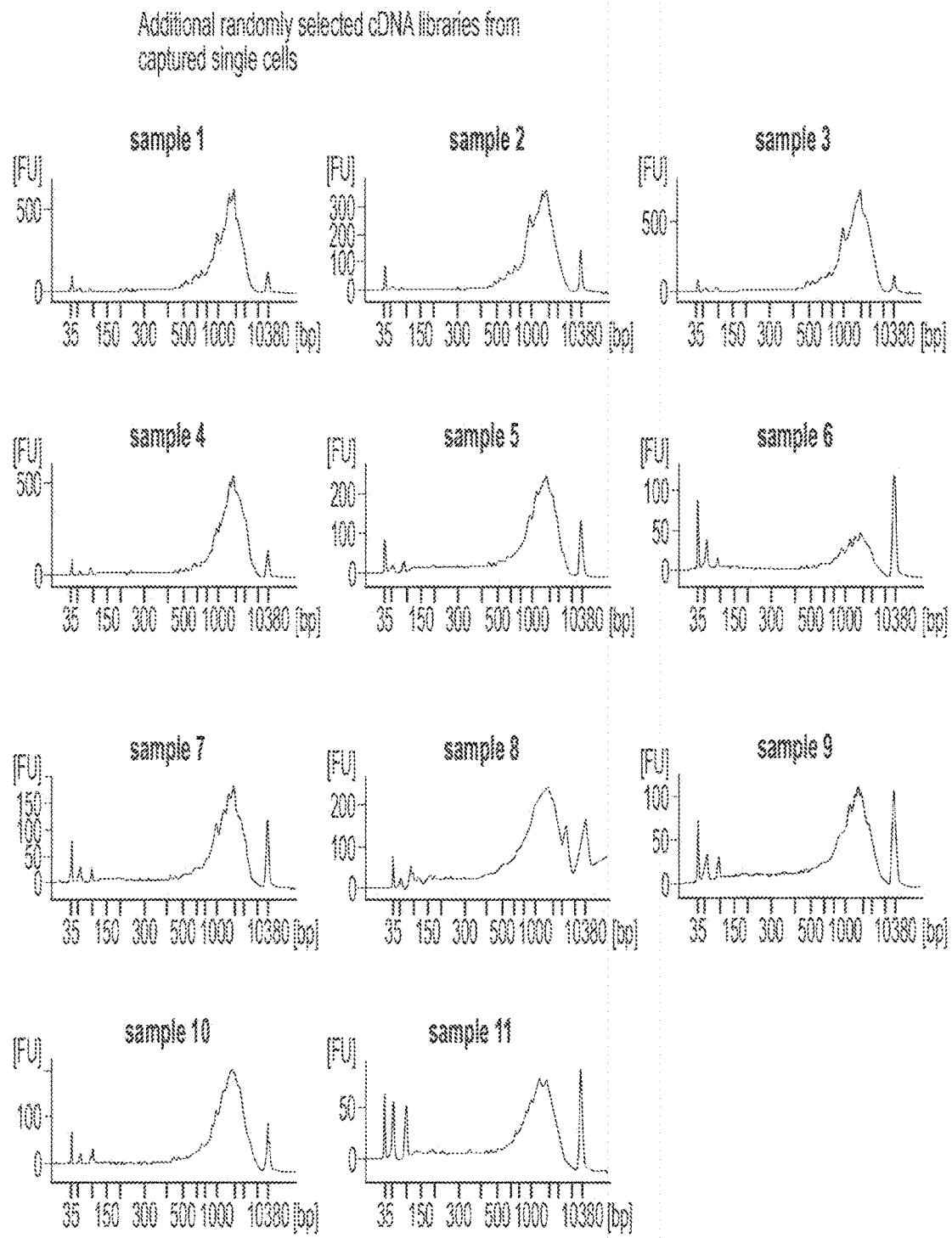
FIG. 7 depicts additional random cDNA libraries from single cells captured by the novel cell capturing system.

FIG. 7 depicts eleven additional random cDNA libraries from single cells captured by the cell capturing system.

Figure 9A:
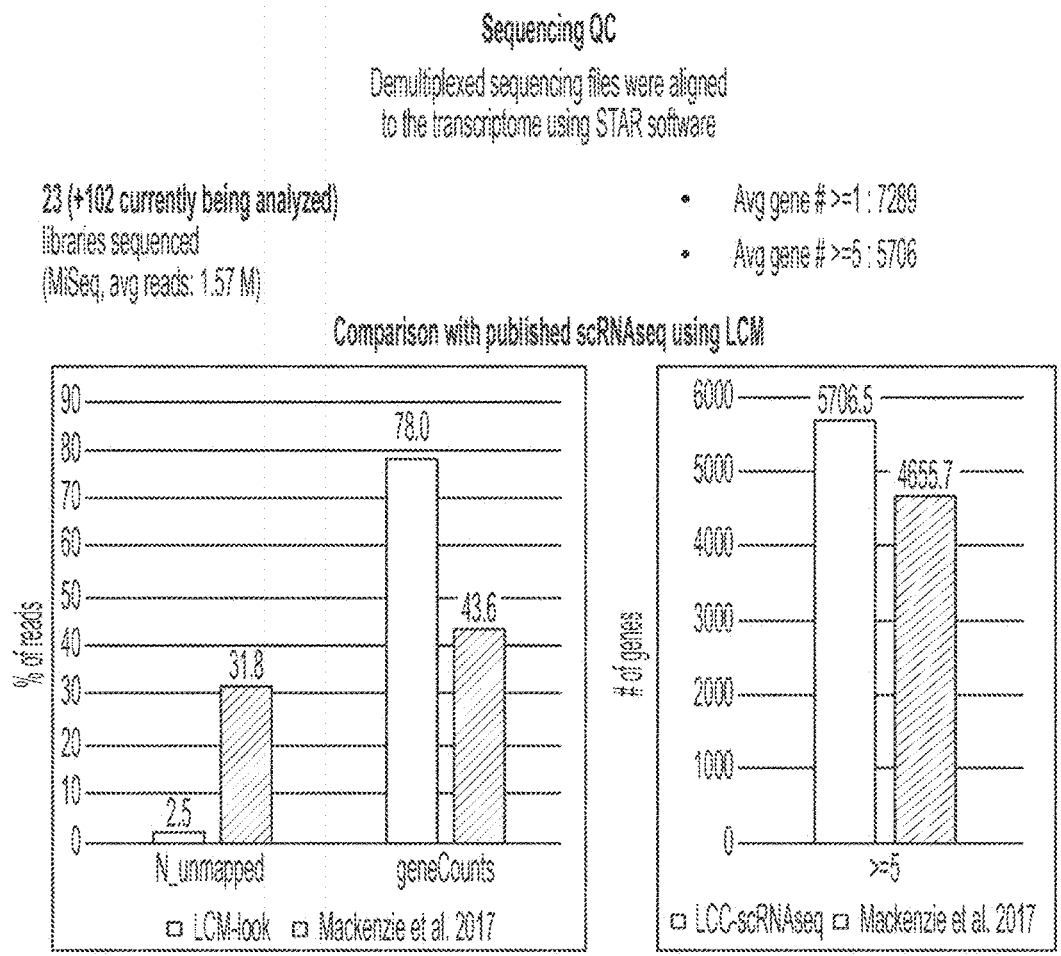

FIGS. 8, 9A, and 9B demonstrate the overall efficiency and robustness of the cell capturing system in generating high quality single-cell RNA sequencing data for human RPE-1 cells. For comparison, Table 1 shown in FIG. 8 shows the percentage of successful generation of cDNA libraries from single cells that were captured by previously known cell capturing methods of single cell sorting or manually separated cells by trypsinization and serial dilution following single cell sorting. Whether or not a generation is successful is assessed by two factors: (1) cDNA library concentration (using Qubit) and (2) cDNA fragment size (using Bioanalyzer).

Table 2A shown in FIG. 8 shows the percentage of successful generation of cDNA libraries from single cells that were captured by the cell capturing system. The table shows a 89% generation success rate (140 successful out of 158). Table 2B shown in FIG. 8 shows the percentage of successful generation of cDNA libraries from single cells that were captured by the cell capturing system, using an increased sample size of 315 samples. The table shows a 91% generation success rate (287 successful out of 315). These high success rates show the robustness of the cell capturing system.

FIG. 9A shows sequencing quality control analysis for single cell RNA sequence quality, which are sequencing metrics after the cDNA libraries are sequenced. A first well-accepted sequencing metric is the number of genes detected, shown on the top right of FIG. 9A. A second well-accepted sequencing metric is the percentage of the reads aligned to the transcriptome and of the unable to align (un-mapped reads). Data from the novel cell capturing system is shown in grey, while data from an existing methodology is shown in black for comparison. The data shown in black is from the Mckenzie et. al in a 2017 Nature paper, and was generated by a conventional Zeiss Palm system of laser capture microdissection using the previously known methodology of removing all cell culture media prior to cell capture and capturing single cells one at a time using one plate per cell.

As shown in FIG. 9A, in terms of sequencing library quality, the novel cell capturing system outperforms the conventional approach used in the Mckenzie et. al in a 2017 Nature paper. The novel cell capturing system also outperforms the Mckenzie et. al in a 2017 Nature paper in the other aspects discussed above as well: robustness, efficiency, high throughput, method timing and ease of difficulty.

FIG. 9B shows sequencing quality control analysis data for a larger sample size of 287 sequenced samples, showing a high number of reads.

Figure 10:
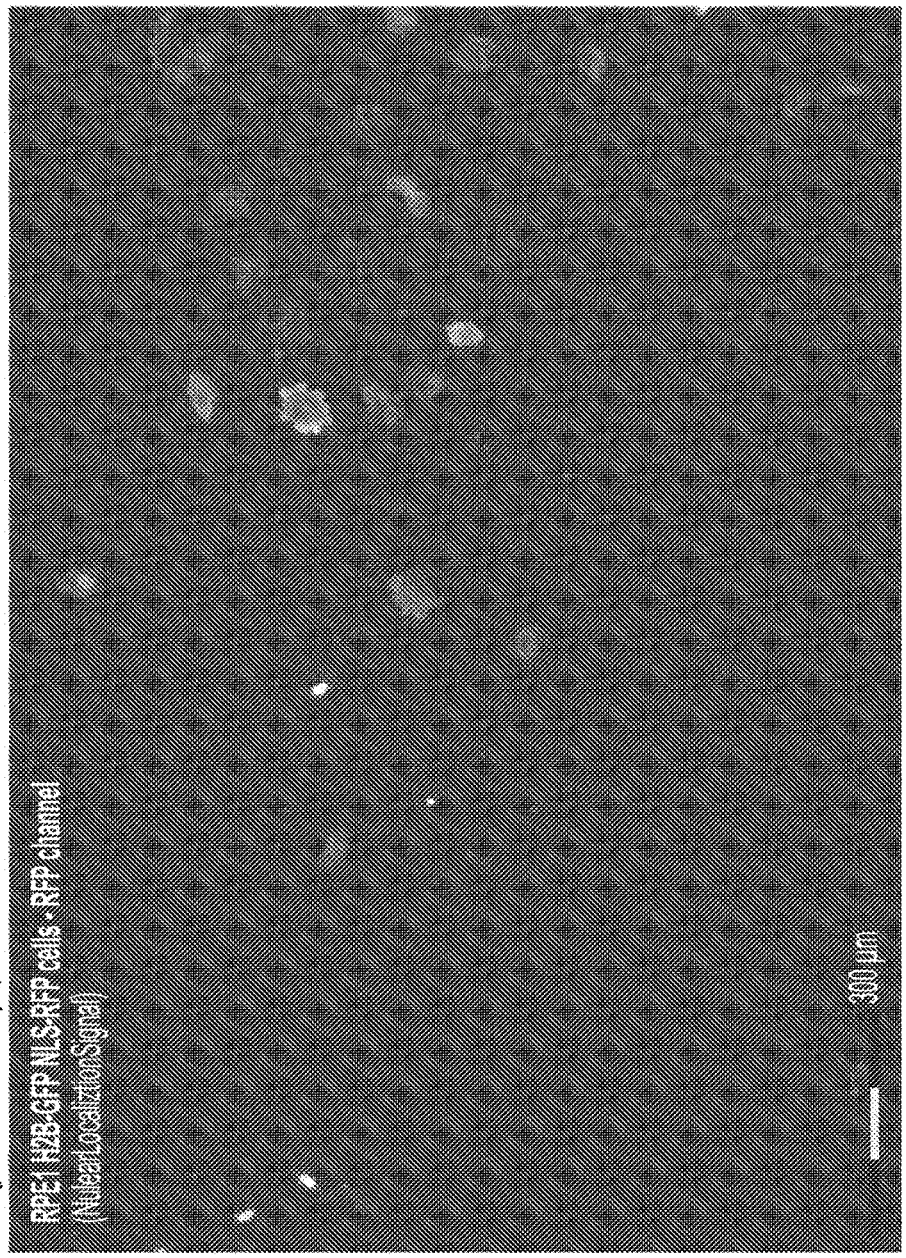
FIGS. 10-12 illustrate how the chamber arrangement of the novel cell capturing system permit the cells to remain healthy before cell capture as compared to previously known methods.
Figure 11:
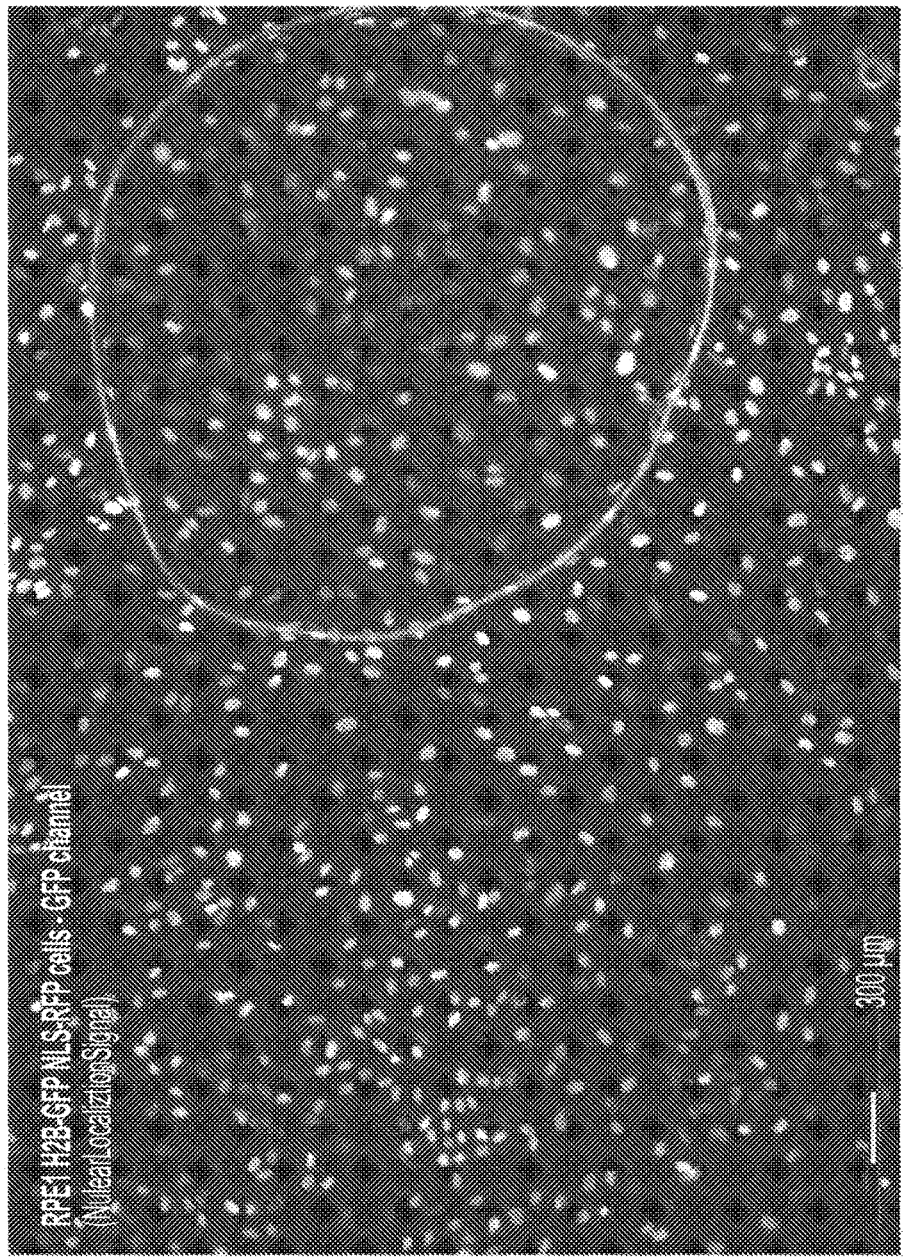
Figure 12:
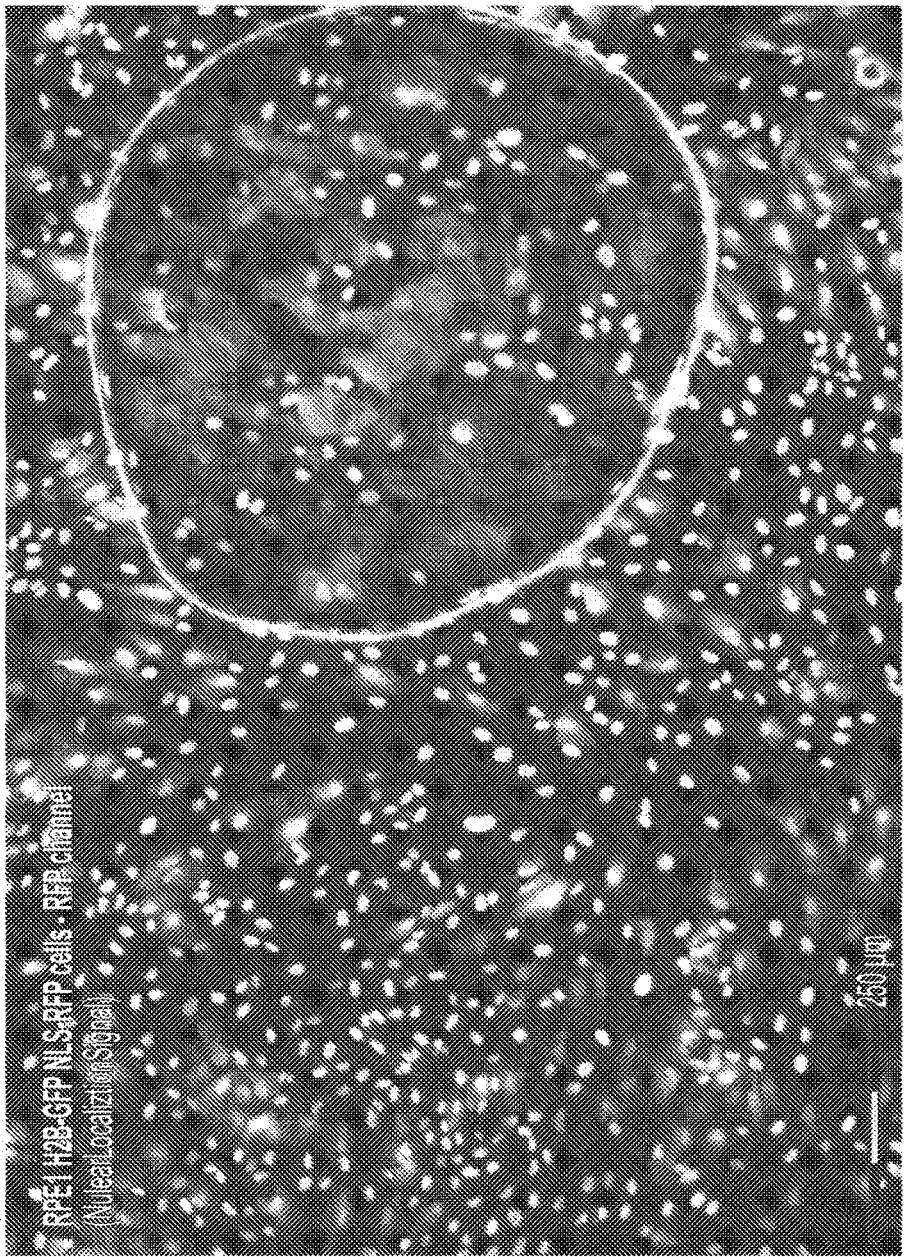
Figure 13:
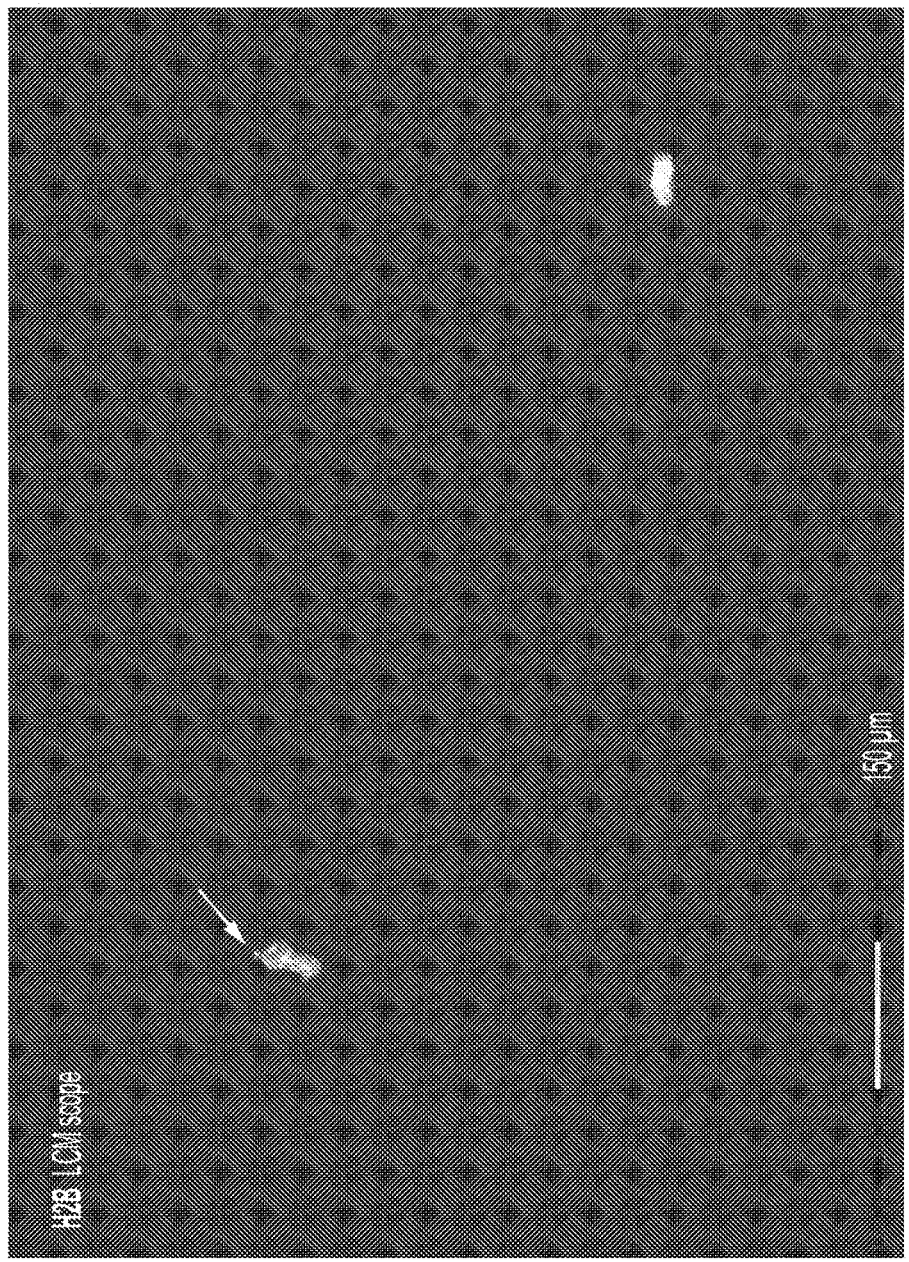
FIGS. 13-14 are images of cells in the chamber of the novel cell capture arrangement.
Figure 14:
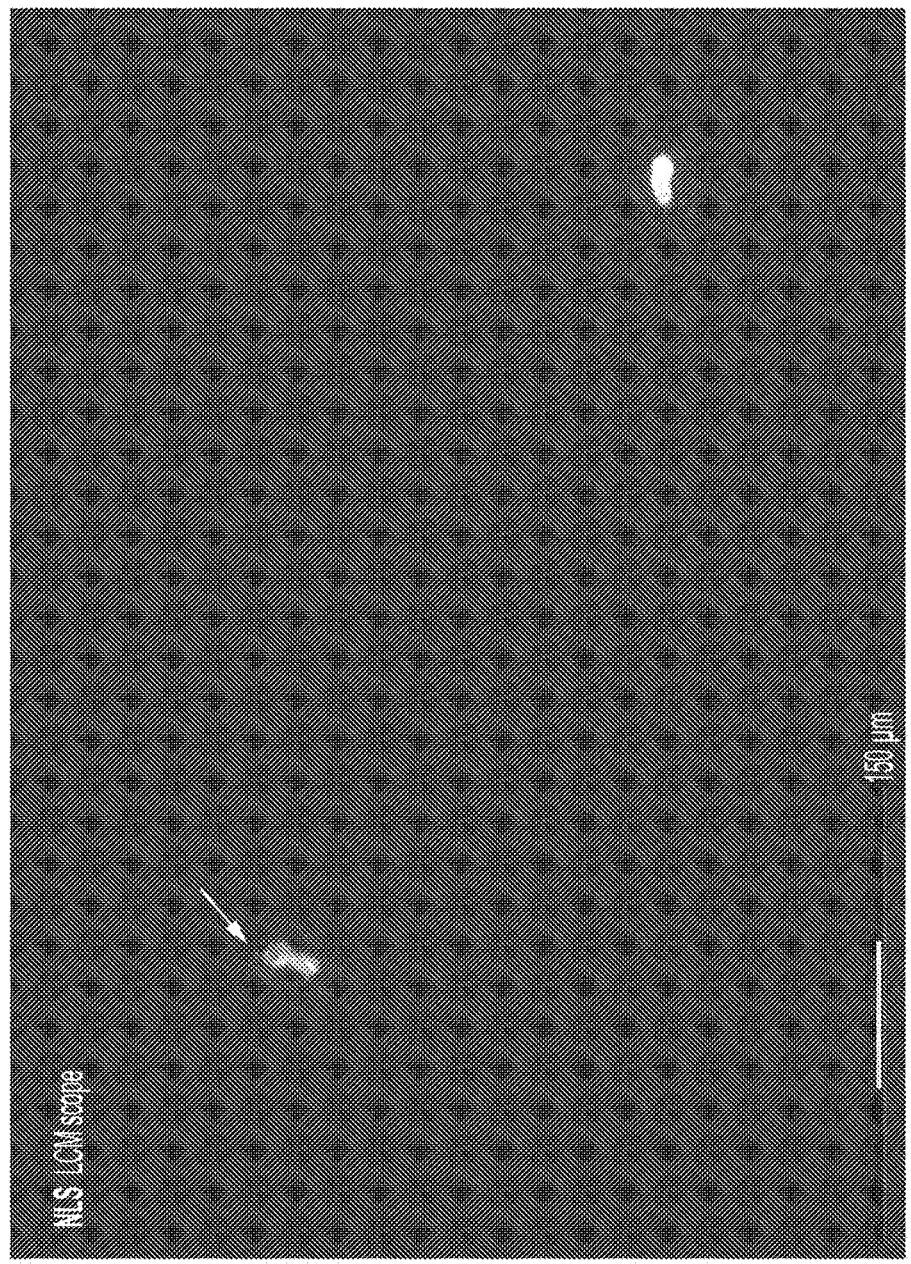

FIGS. 10-12 illustrate how the chamber arrangement of the novel cell capturing system permits the cells to remain healthy before cell capture as compared to previously known methods. FIG. 10 is an image of cells in the chamber showing the occurrence of cell death using previously known cell capturing techniques. The image was taken from the red fluorescence channel of the laser capture microdissection microscope and shows the NLS-RFP of the cells that are cytoplasmic (the normal localization of NLS is nuclear), indicating fracture of the nucleus and disturbed cell homeostasis and death. One possibility for the cell death may be due to the step of removing cell culture media before cell capture, as required by conventional cell capture protocols.

FIGS. 11-14 are images of cells in the chamber of the novel cell capture arrangement. The image for H2B-GFP (showing histones/chromatin, the nucleus structures of the cells showing basically the cells on the culture) and the NLS-RFP that were used as a viability (nucleus integrity) marker shows that the cells are viable more than 90 minutes after being set up in the chamber and with the microscope. A small air bubble was purposefully formed and captured in the image to show the difference between the live, viable cells outside the bubble and the dying cells inside the air bubble. Note that the air bubble was purposefully introduced into the chamber and can normally be easily avoided.

In some embodiments, cells are first imaged in an imaging microscope to identify cells of interest and/or to determine important information associated with such cells, and then transferred to a cell capturing device such as a laser capture microdissection device. In some embodiments, the scope of the cell capturing device is insufficient to identify cells of interest and/or unable to gather important pieces of information that an imaging device, e.g. a fluorescent microscope, can. In some embodiments, a user may flag or otherwise identify cells of interest in a software program while using the imaging microscope. The software program may save the coordinates that identify the locations of the flagged cells. The coordinates may be sent to, loaded into, or otherwise obtained by the cell capturing device, and the cells are moved from the imaging microscope to the cell capturing device. Using the coordinates from the imaging microscope, the cell capturing device is able to identify and highlight for a user the previously flagged cells of interest. In some embodiments, the coordinates from the imaging device are converted for compatibility with the cell capturing device.

In some embodiments, predefined marks (74) may be present on the cell chamber, e.g. on an adapter or other portion of the chamber. These marks may be used to define coordinates to help identify the location of the cells of interest after the cells are moved from an imaging microscope to a cell capture device (e.g. laser dissection microscope).

Figures 15A, 15B:
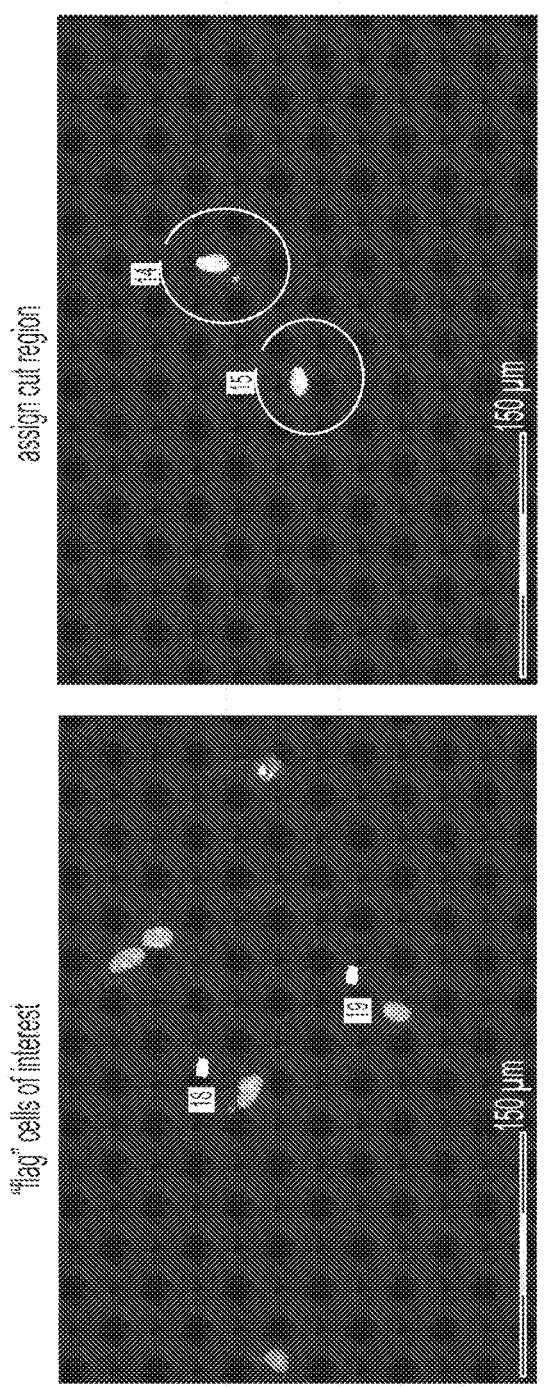
FIGS. 15A and 15B show images demonstrating a process of identifying cells of interest and assigning cut regions for those cells.

FIGS. 15A and 15B show images demonstrating a process of identifying cells of interest and assigning cut regions for those cells while the cells are imaged using an imaging microscope such as a fluorescent microscope. As shown in FIG. 15A, cells of interest are "flagged." As shown in FIG. 15B, a cut region around those cells of interest are then assigned. A user may manually assign a cut region, or the software may automatically determine an appropriate cut region. The coordinates of the cut region may then be obtained by a cell capturing device, e.g. a laser capture microdissection instrument, that will be used to dissect and capture these cells of interest.

A side-by-side comparison of cells viewed under an imaging microscope versus the same cells viewed under a laser capture microdissection device is shown in FIGS. 16A and 16B. FIG. 16A shows an image taken from a fluorescence microscope, where three cells of interest are indicated. FIG. 16B shows an image taken from a laser capture microdissection scope, where the three cells of interest are flagged.

Figure 17:
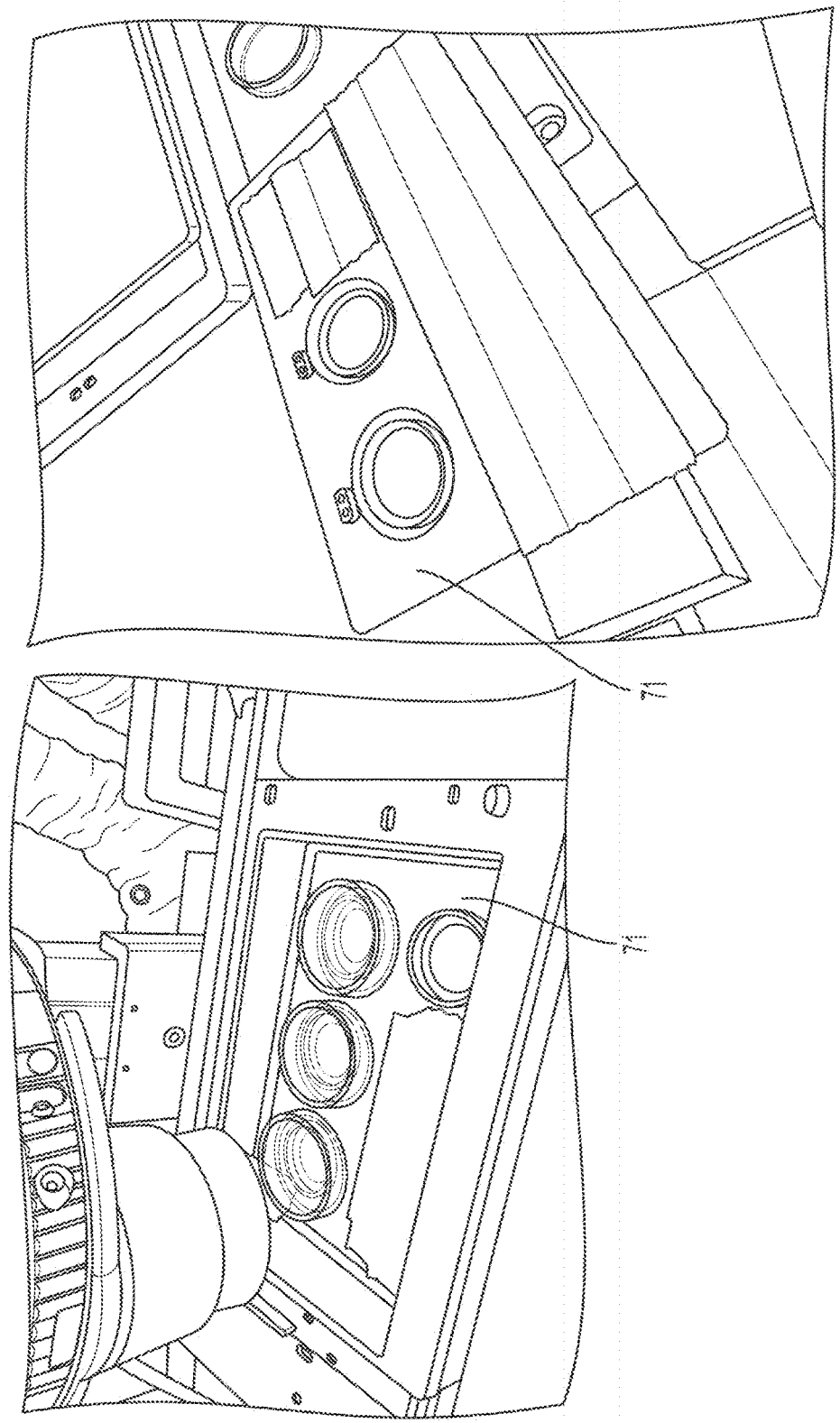
FIG. 17 shows images of a setup used for imaging of live cultures.

FIG. 17 is an image of a setup used for imaging of live cultures in a laser capture microdissection device. In some embodiments, an adapter may be used to permit use of the chamber arrangement described above with existing laser capture microdissection microscopes. In some embodiments, an adapter can hold more than one chamber at a time. FIG. 17 shows illustrative embodiments of adapters 71 each having multiple receptacles, where each receptacle is configured to receive and hold a chamber.

Figure 18:
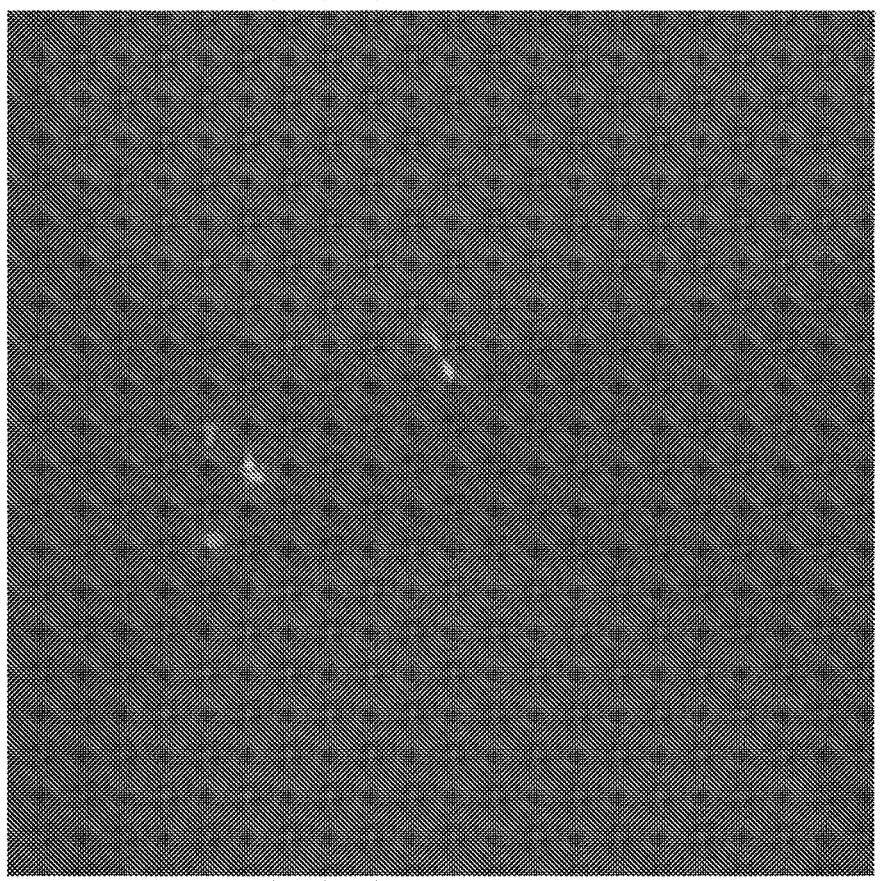
FIGS. 18-20 are images taken from imaging microscopes.
Figure 19:
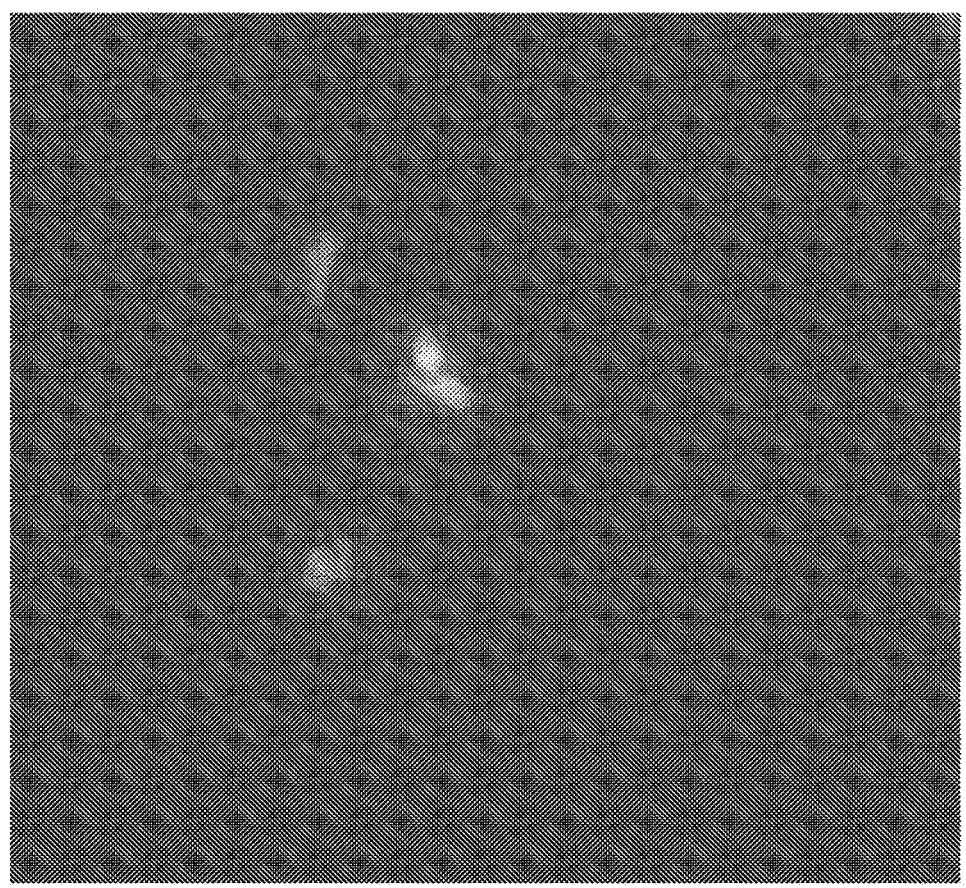
Figure 20:
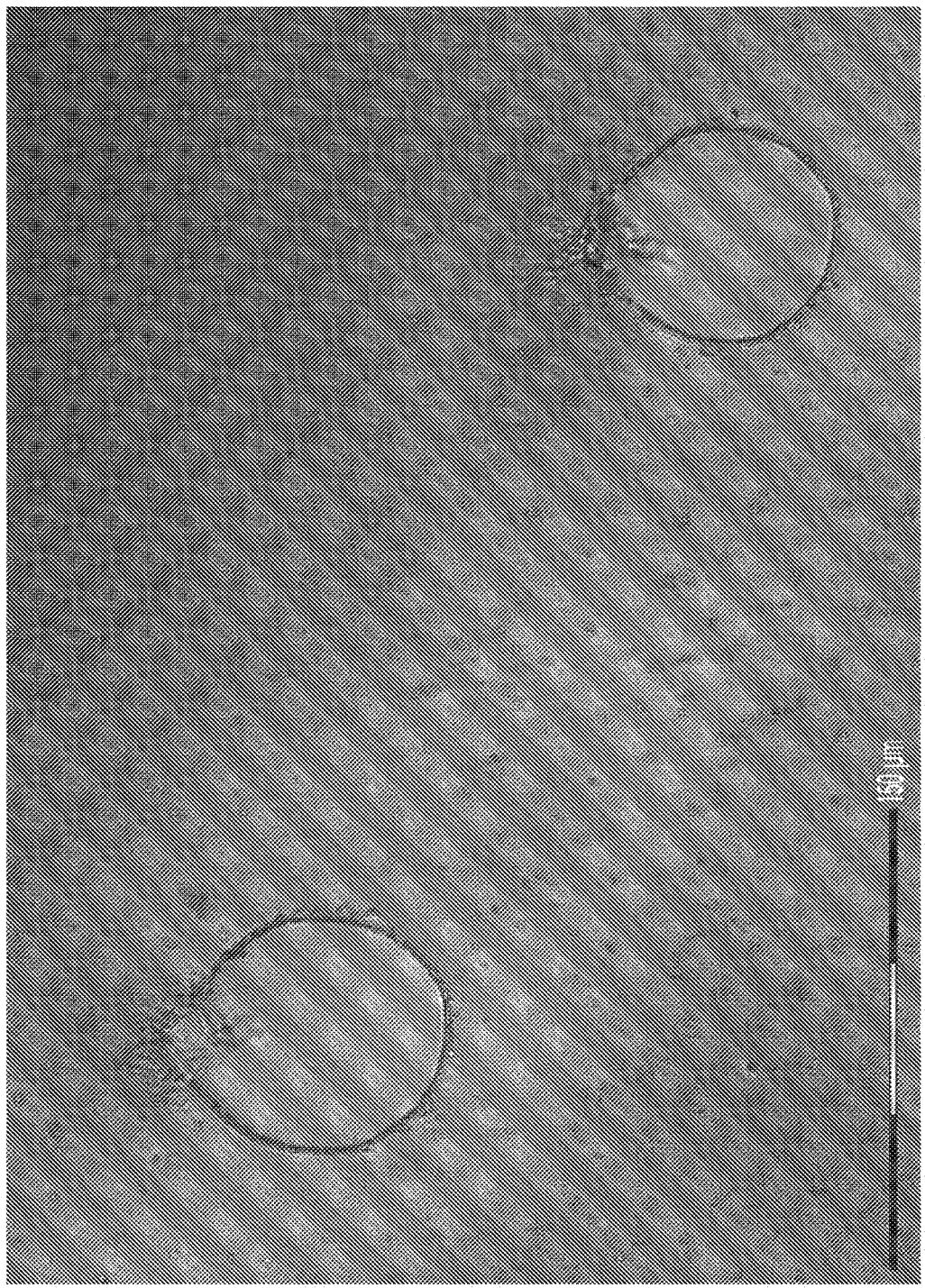

FIGS. 18, 19, and 20 are images taken from imaging microscopes, in which cells in the chamber arrangement are directly imaged while the cells are in the chamber. FIGS. 18 and 19 are taken from a fluorescent microscope, where FIG. 19 is a zoomed-in version of FIG. 18.

In some embodiments, the chamber and laser capture microdissection arrangement may be used to capture single cells or nuclei from confluent cultures or attached cells. In some embodiments, a cytoplasmic fluorescent marker may be used to define the cell borders of a cell of interest.

Figure 21B:
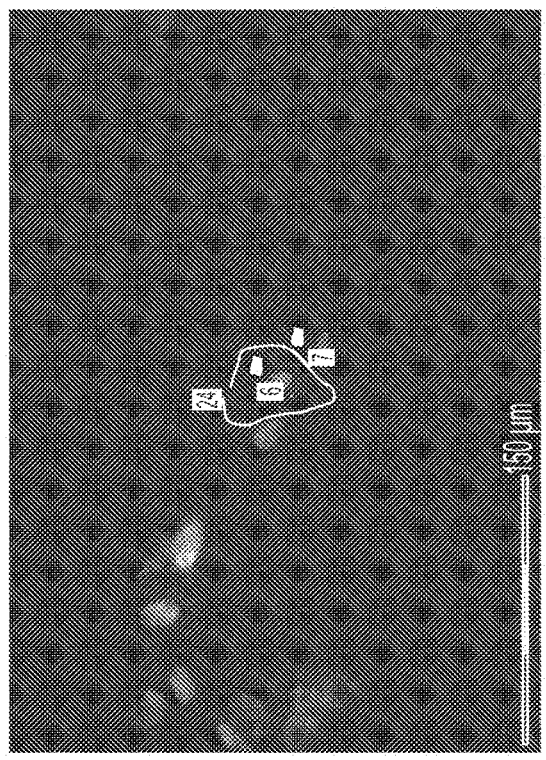
FIG. 21B shows an identified cell border viewed under a laser capture microdissection scope.
Figure 21A:
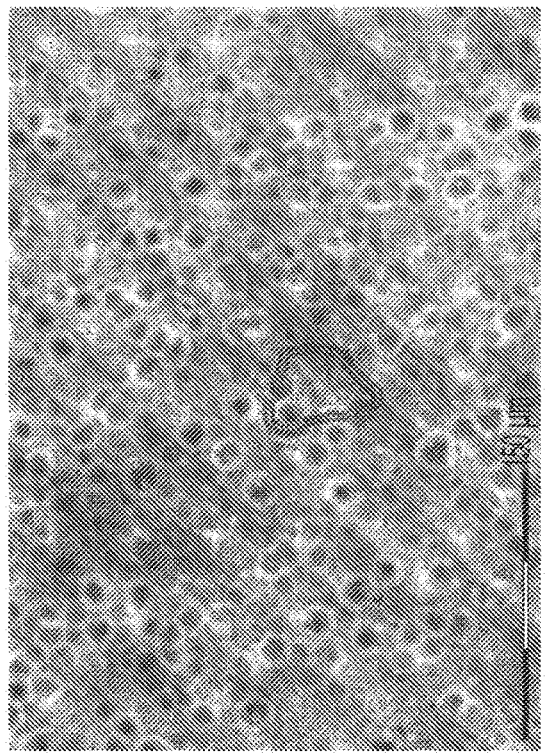
FIG. 21A is an image taken from a fluorescent microscope, with items of interest flagged.

FIG. 21A shows an image taken from a fluorescent microscope, with items of interest flagged, including an identification of a nucleus and a cell border. FIG. 21B shows the identified cell border viewed under the laser capture microdissection scope.

In some embodiments, the chamber and laser capture microdissection arrangement may be used for single-cell DNA sequencing. Studies were conducted to demonstrate the performance of the cell capturing system for use with single-cell DNA sequencing. Single cells were isolated from live cultures using the chamber arrangement described above and a laser capture microdissection instrument. Single-cell sequencing was conducted using Whole Genome Amplification using the Multistrand Displacement Amplification method from QIAGEN, and Illumina sequencing was performed. The resulting data is shown in FIGS. 22 and 23, which demonstrate the overall efficiency and robustness of the cell capturing system in generating high quality single-cell DNA sequencing data.

In Table 3 shown in FIG. 22, the "Total DNA" column shows the total DNA yield after Whole Genome Amplification, which indicates the efficiency of the process. In Table 4 in FIG. 23, "PCT_PF_READS_ALIGNED" is the percentage of unique reads aligned to the genome, and "PCT_CHIMERAS" is the percentage of chimera reads. These two results indicate the high quality of the process.

In some embodiments, the chamber and laser capture microdissection arrangement may be used in a re-culturing application in which live single cells of interest are captured and transferred from an initial culture to another independent culture. Such a method may be used, for example, to generate and expand single-cell clones starting from initial cells of interest.

Figure 24A:
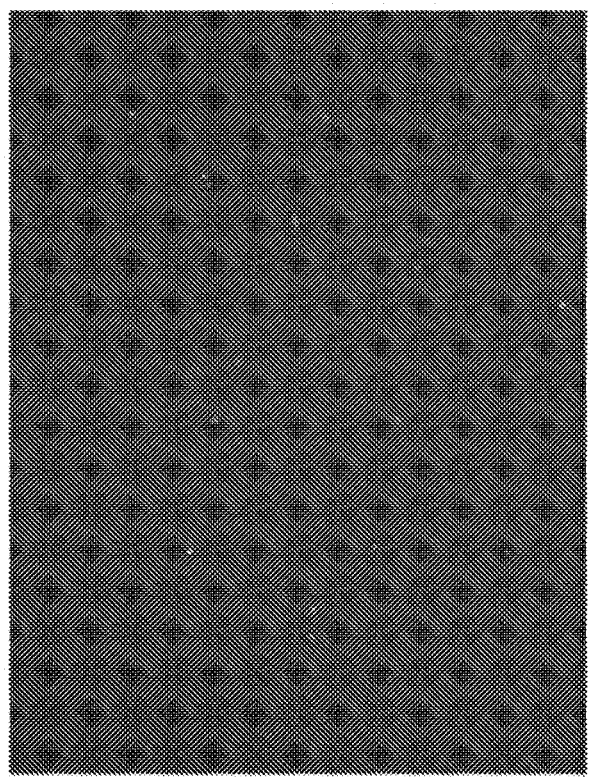
FIGS. 24A and 24B show images of the resulting cells about 80 hours after re-culturing, expressing fluorescent markers.
Figure 24B:
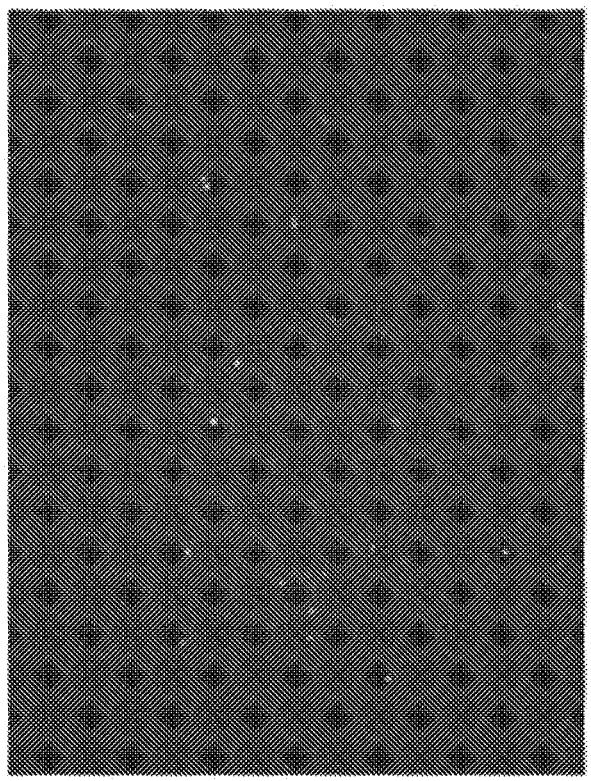
Figure 25B:
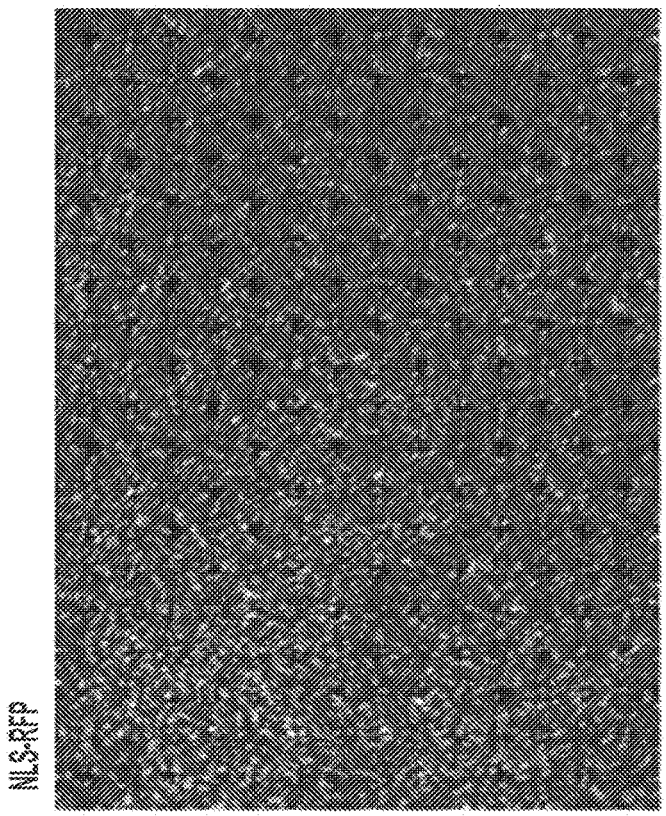
FIGS. 25A and 25B show images of the resulting cells 17 days after re-culturing.
Figure 25A:
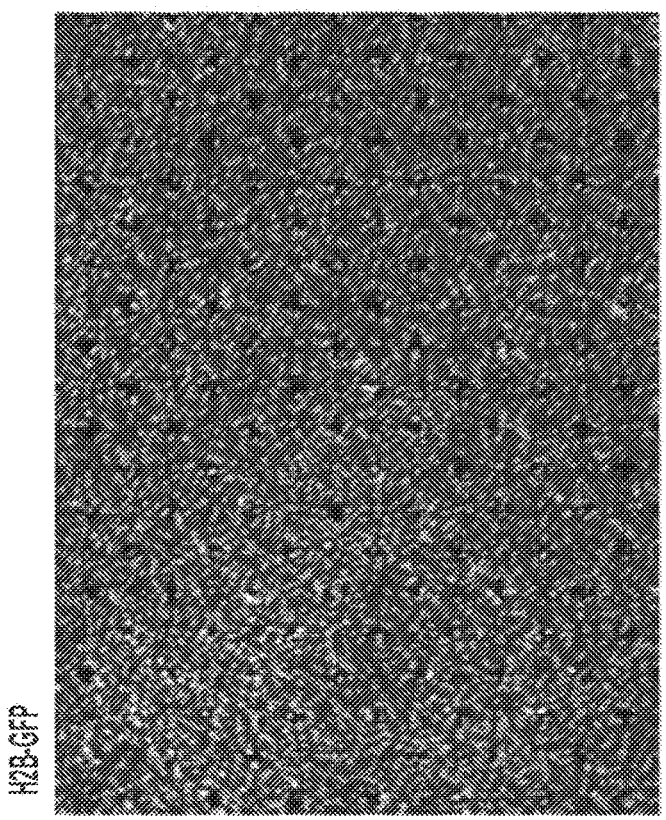

In one study, RPE-1 H2B-GFP NLS-RFP cells were cultured and single cells were isolated using a chamber and laser capture microdissection arrangement. The captured cells were transferred to 96-well imaging plates. About 80 hours after the transfer, imaging the imaging plates showed that the resulting cells were expressing fluorescent markers, as shown in FIGS. 24A and 24B, indicating that the cells were alive and physiologically normal. The images were taken at 5× magnification. About 17 days after the transfer, imaging the imaging plates showed that the cells had proliferated and were expressing fluorescent markers, as shown in FIGS. 25A and 25B, indicating that the cells were alive and physiologically normal.

Figure 26:
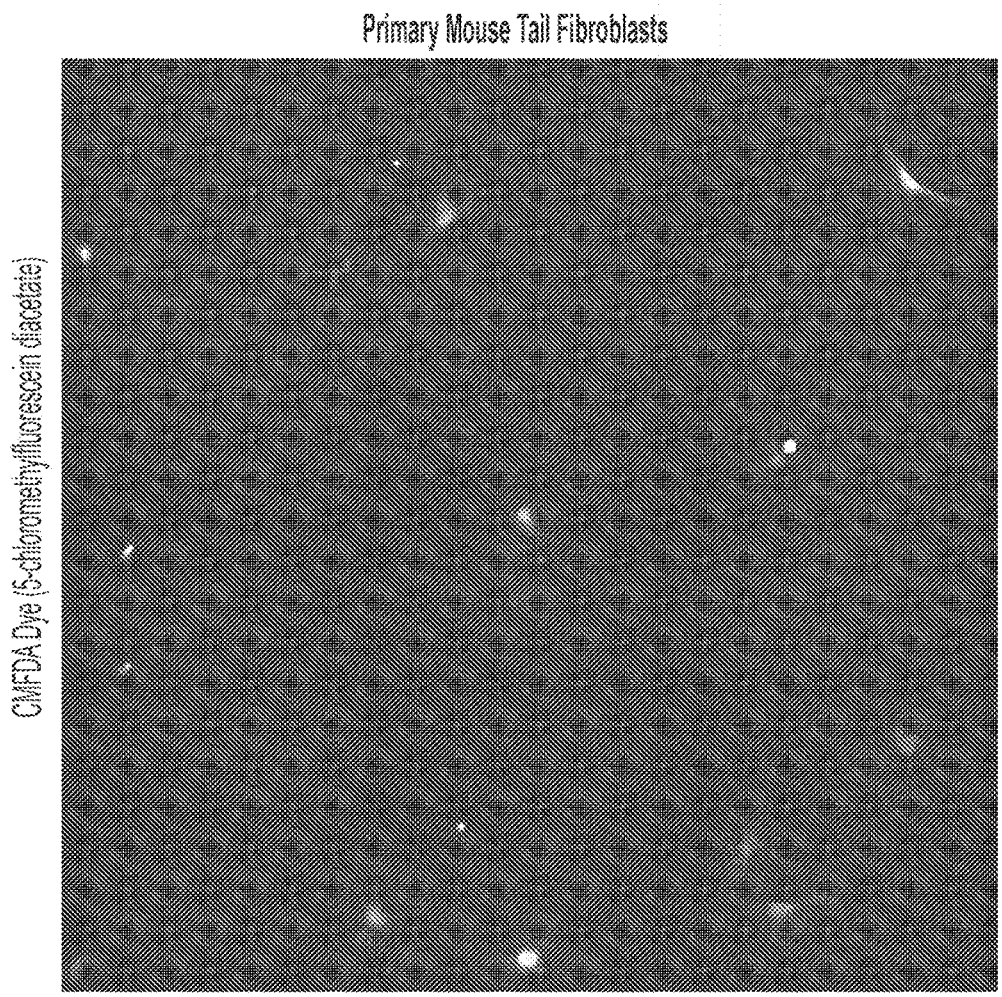
FIG. 26 shows an image of primary mouse tail fibroblasts taken by a fluorescent microscope.

As discussed above, different cell types and cells lines may be used with the arrangements and methods described herein. In one example, primary mouse tail fibroblasts shown in the image of FIG. 26 were used with one embodiment of a cell capturing system described above. The image is shown in 20× magnification, with 9 images stitched together in a 3×3 layout. Table 5 shown in FIG. 27 shows resulting data that demonstrate the overall efficiency and robustness of the cell capturing system in generating high quality sequencing data for primary mouse tail fibroblasts. The second column is the percentage of the un-mapped reads and the third column is the percentage of reads aligned to the transcriptome. The last four columns are the number of genes detected.

While the present teachings have been described in conjunction with various embodiments and examples, it is not intended that the present teachings be limited to such embodiments or examples. On the contrary, the present teachings encompass various alternatives, modifications, and equivalents, as will be appreciated by those of skill in the art. Accordingly, the foregoing description and drawings are by way of example only.

What is claimed is:

1. A system for capturing one or more cells of interest from a plurality of cells, comprising:
    a cell culture membrane;
    cell culture media;
    a plurality of cells on the cell culture membrane and positioned within the cell culture media;
    a transparent surface in contact with the cell culture media, the cell culture media being positioned between the cell culture membrane and the transparent surface;
    a microscopic imaging device;
    a collector positioned closer to the cell culture membrane than to the transparent surface; and
    a laser source positioned closer to the transparent surface than to the cell culture membrane.

2. The system of claim 1, wherein the transparent surface comprises a glass coverslip.

3. The system of claim 1, further comprising a ring coupled to the cell culture membrane, wherein the ring, the cell culture membrane and the transparent surface form a chamber for holding the cell culture media.

4. The system of claim 1, further comprising a hydrophobic barrier.

5. The system of claim 3, further comprising a hydrophobic barrier applied to a surface of an inner periphery of the ring.

6. The system of claim 1, wherein the collector comprises a multi-well plate.

7. The system of claim 3, wherein the cell culture membrane spans the ring.

8. The system of claim 3, wherein the chamber includes a mark configured to define coordinates of locations of one or more cells of interest.

9. The system of claim 1 wherein the collector does not attach to the cell culture membrane.

10. A method of capturing one or more cells of interest from a plurality of cells, comprising:
    providing a plurality of cells that are on a cell culture membrane and in cell culture media;
    covering the plurality of cells and the cell culture media with a transparent surface such that the cell culture media is positioned between the cell culture membrane and the transparent surface;
    imaging the plurality of cells with an imaging device; and
    shining a laser beam through the transparent surface to cut out one or more cells of interest from the plurality of cells while the plurality of cells are within cell media, causing the one or more cells of interest from the plurality of cells to move in a direction away from the transparent surface onto a collector.

11. The method of claim 10, further comprising flipping the plurality of cells upside down such that the cell culture membrane is positioned above the transparent surface.

12. The method of claim 10, wherein the collector is positioned above the transparent surface.

13. The method of claim 10, wherein the one or more cells of interest from the plurality of cells comprises only a single cell.

14. The method of claim 10, wherein the one or more cells of interest from the plurality of cells comprises five cells or less.

15. The method of claim 10, further comprising re-culturing the one or more cells of interest from the plurality of cells.

16. The method of claim 10, further comprising imaging the plurality of cells with a fluorescent microscope and then moving the plurality of cells to the imaging device.

17. The method of claim 10, further comprising:
    marking one or more cells of interest while imaging the plurality of cells with a fluorescent microscope;
    identifying the coordinates of the marked one or more cells of interest;
    moving the plurality of cells to a cell capturing device; and
    identifying said coordinates while imaging the plurality of cells with the imaging device of the cell capturing device.

18. The method of claim 10, wherein the plurality of cells remain in the cell culture media during the laser cutting process.

19. The method of claim 10, wherein the one or more cells of interest remain alive.

20. A chamber for capturing one or more cells of interest from a plurality of cells, comprising:
    a ring;
    a cell culture membrane coupled to the ring; and
    a transparent surface opposing the cell culture membrane to form a watertight chamber with the ring and the cell culture membrane; and
    further comprising a hydrophobic barrier;
    wherein the hydrophobic barrier is applied to a surface of an inner periphery of the ring.

21. The chamber of claim 20, wherein the transparent surface comprises a glass coverslip.

\* \* \* \* \*